United States Patent [19]
Moodley

[11] Patent Number: 5,380,203
[45] Date of Patent: Jan. 10, 1995

[54] DENTURES AND METHOD OF MANUFACTURING SAME

[76] Inventor: Sundru M. Moodley, 610 S. Harrison La., Denver, Colo. 80209

[21] Appl. No.: 185,505

[22] Filed: Jan. 24, 1994

[51] Int. Cl.$^6$ .............................................. A61C 13/08
[52] U.S. Cl. ..................................... 433/198; 433/197
[58] Field of Search ............... 433/167, 197, 198, 206, 433/207, 208, 209, 210, 211, 171

[56] References Cited

U.S. PATENT DOCUMENTS

| | | | |
|---|---|---|---|
| 1,681,436 | 8/1928 | Sears | 433/197 |
| 2,129,040 | 9/1938 | Sears . | |
| 2,295,864 | 9/1942 | Prange . | |
| 2,375,509 | 5/1945 | Wiechert . | |
| 2,397,407 | 3/1946 | Butler . | |
| 2,528,629 | 11/1950 | Wiechert . | |
| 2,548,956 | 4/1951 | Dickson | 433/197 |
| 2,549,636 | 4/1951 | Raber . | |
| 2,570,562 | 10/1951 | Kinsley | 433/197 |
| 2,669,021 | 2/1954 | Bader . | |
| 2,717,445 | 9/1955 | Ford | 433/198 |
| 2,741,845 | 4/1956 | Appenrodt et al. | 433/197 |
| 2,874,487 | 2/1959 | Bloom et al. . | |
| 3,252,220 | 5/1966 | Goddard . | |
| 3,305,926 | 2/1967 | Gerber . | |
| 3,583,070 | 6/1971 | Nietert et al. . | |
| 3,638,309 | 2/1972 | Frush . | |
| 4,525,146 | 6/1985 | Lewis et al. | 433/198 |

FOREIGN PATENT DOCUMENTS 732133  6/1955  United Kingdom .

*Primary Examiner*—Gene Mancene
*Assistant Examiner*—Nicholas D. Lucchesi
*Attorney, Agent, or Firm*—Holland & Hart

[57] ABSTRACT

Dentures of the present invention include opposing upper and lower dentures and have at least one pair of opposing upper and posterior lower artificial teeth. Each posterior upper artificial tooth is formed from a resilient material, preferably an acrylic material, and has a substantially flat masticating surface. Each posterior lower artificial tooth has a single longitudinal crest formed along the length of its masticating surface. An elongated metal blade is embedded in each posterior lower artificial tooth with a longitudinal edge of the metal blade lying flush with the longitudinal crest. The dentures are manufactured by aligning the metal blade and longitudinal crest of each posterior lower artificial tooth substantially parallel with and overlying the apex of denture wearer's mandibular ridge and by aligning each opposing posterior upper artificial tooth substantially parallel with and centrally overlying the denture wearer's maxillular ridge.

19 Claims, 3 Drawing Sheets

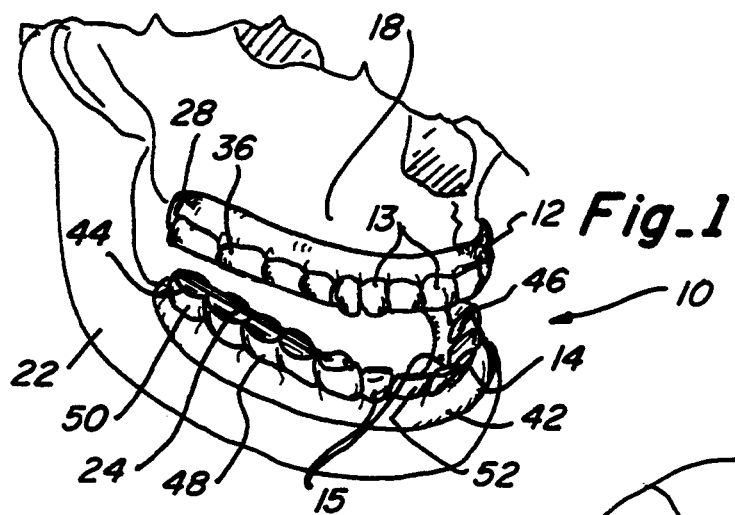
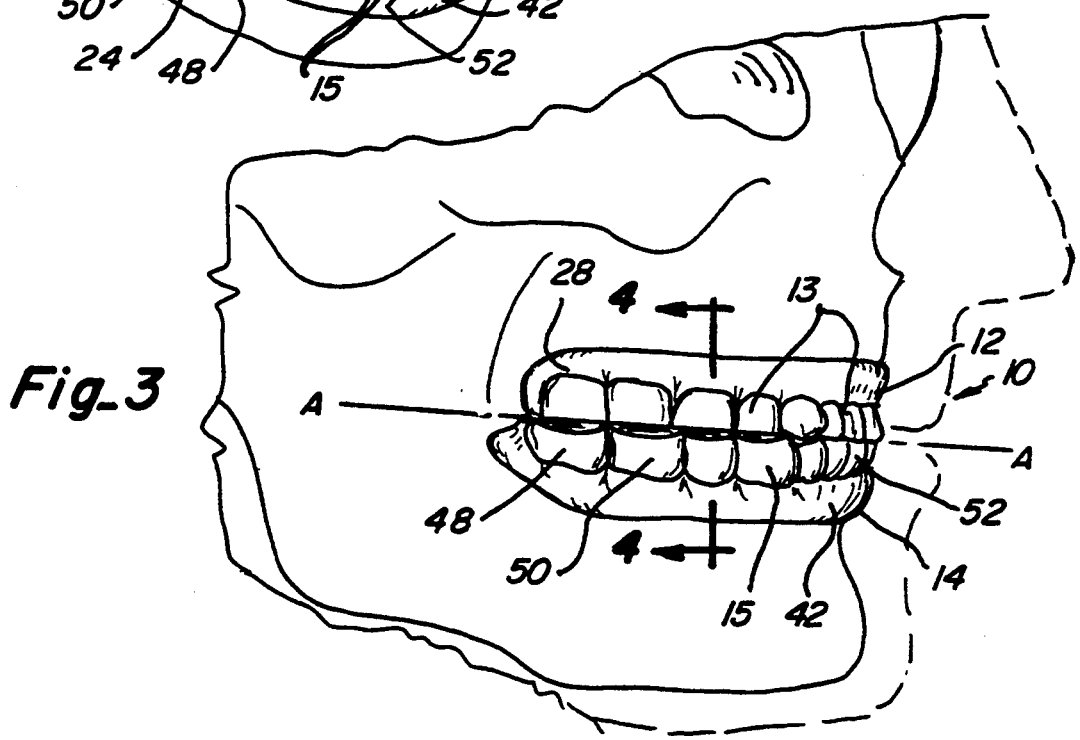
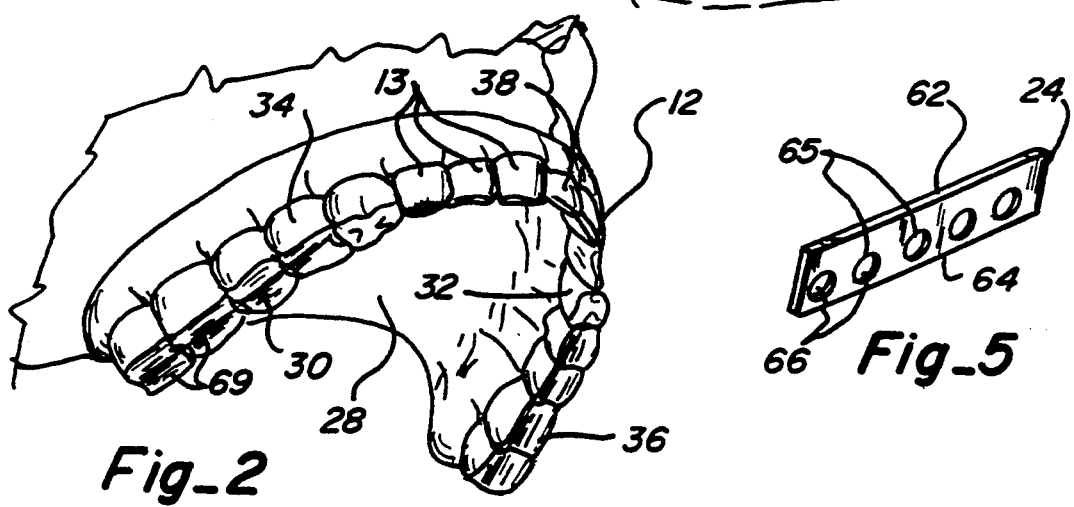
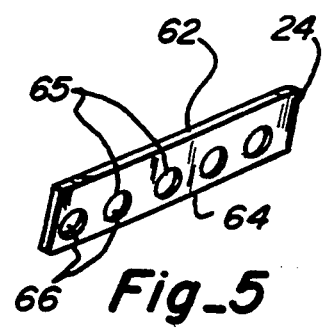

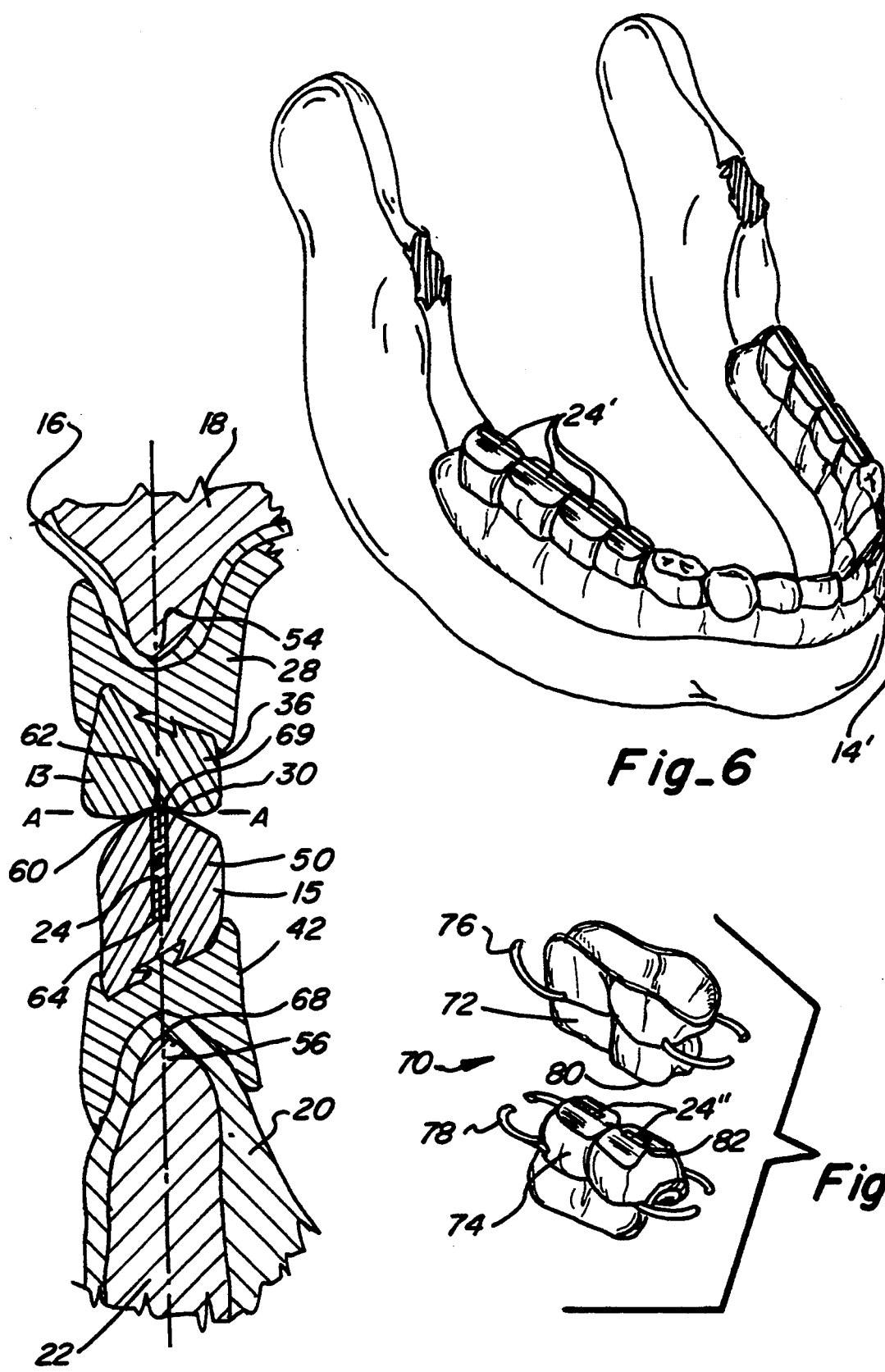

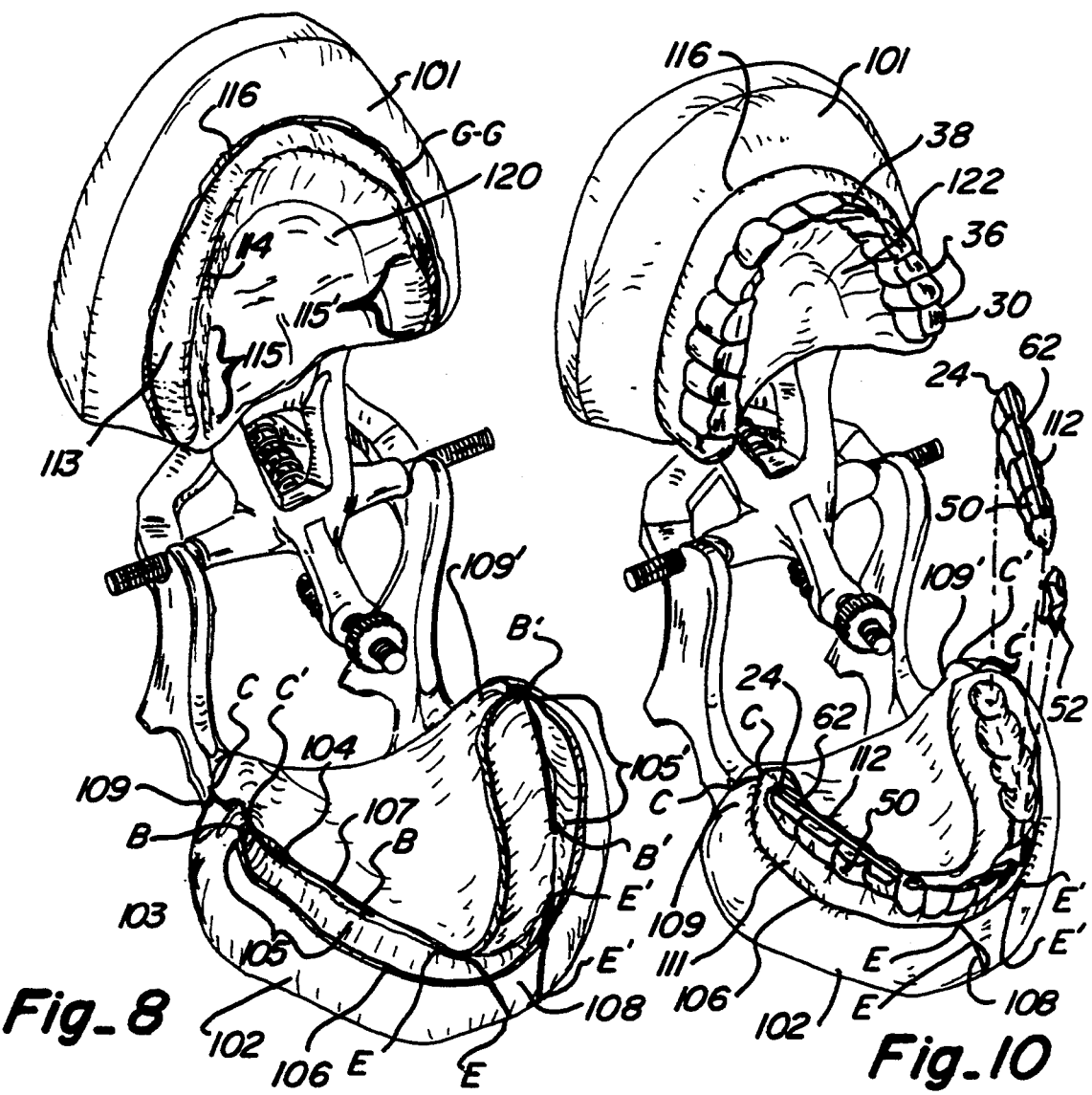
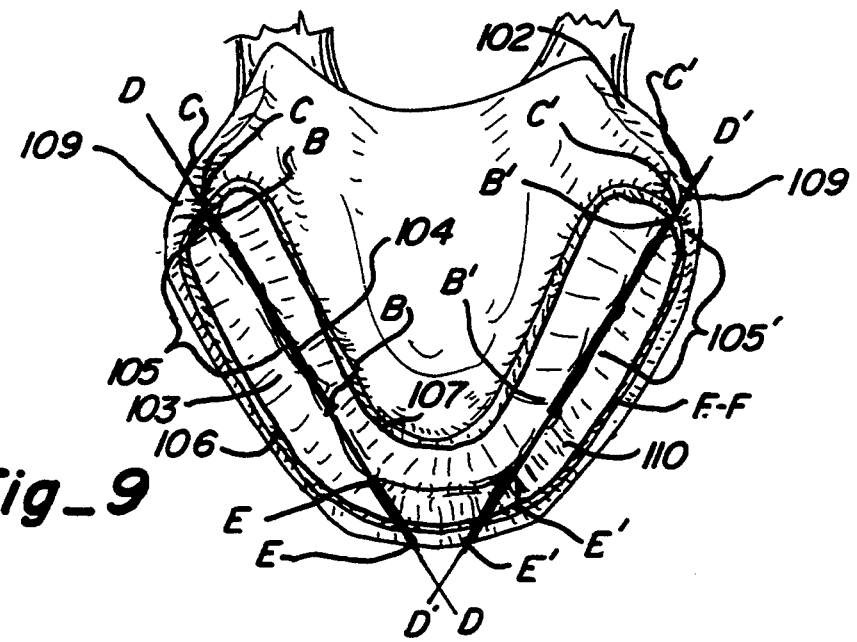
Fig_8  Fig_9  Fig_10

DENTURES AND METHOD OF MANUFACTURING SAME

FIELD OF THE INVENTION

This invention relates to dentures and more particularly to new and improved opposing upper and lower dentures which exhibit increased stability and comfort in use and which are easier to manufacture and fit to a denture wearer.

BACKGROUND OF THE INVENTION

In the past, dentures have been made to closely resemble the size and shape of natural teeth. Unlike natural teeth, however, dentures are not permanently secured to the denture wearer's jaw. As a result, dentures designed to look and function like natural teeth do not have the inherent stability of natural teeth.

In particular, lateral movement of the lower jaw relative to the upper jaw is more easily accommodated in natural teeth because of the permanent attachment of the teeth to the lower jaw. During mastication with natural teeth, the central fossa of the lower molars cooperates with the functional cusp of opposing upper molars in a mortar and pestle-like action. When these shapes are copied into artificial dentures, the lower teeth tend to move, tip, or otherwise dislodge as the functional cusp of the upper molars slides outward toward the buccal side of the lower molars.

Protrusive movement of the lower jaw can also be problematical for denture wearers. Especially when the multiple ridges and troughs of natural teeth are formed in the artificial teeth of dentures, blocking or tripping of opposing teeth is often experienced during protrusive movement of the lower jaw.

Unexpected movement of dentures, such as the sliding, tipping, tripping, blocking and dislodging described above, creates serious problems for denture wearers. For example, denture wearers sometimes avoid the company of others because of embarrassment relating to removal of their dentures or lack of control over their dentures. Also by way of example, sore spots may develop on the gums of denture wearers as a result of non-uniform pressure points and/or uncontrolled denture movement. Once sore spots develop, they are further aggravated by denture movement. To minimize pain from these sore spots denture wearers sometimes avoid eating certain foods, creating dietary imbalances and other health problems. The existence of sore spots and continued discomfort may also cause denture wearers to remove their dentures for extended periods of time. When dentures are worn erratically, the original fit of the denture can be lost, in part because of the shrinkage of the wearer's gums. Once the original fit is lost, the incidence and extent of sore spots increase, with the fit of the dentures deteriorating steadily further.

Even when the chewing surfaces of artificial teeth of dentures are not made to look like natural teeth, dental professionals can find it difficult to achieve a satisfactory fit with new dentures. The more complex the shape of artificial dentures, the more difficult such dentures are to fit to a patient. Even after multiple adjustment appointments with the dental professional, malocclusion problems persist in upwards of 85-90% of new denture wearers. Whether or not malocclusion problems are solved, the need for multiple adjustment appointments increases significantly the cost of fitting dentures.

When upper and lower dentures meet in a chewing motion, opposing force is applied to each of the upper and lower dentures. Because the lower denture of a full mouth denture set contacts approximately one-third the gum surface area as compared to the gum surface area contacted by the opposing upper denture of a full mouth denture set, approximately three times the pressure is placed on the lower jaw as compared to the pressure placed on the upper jaw. This increased pressure on the lower denture and jaw creates sore spots and causes undesired movement of the lower denture, in part because of the inability of the surface tension created by saliva between the gum and lower denture to maintain the lower denture in position.

To increase denture stability, some dental professionals align the artificial teeth of lower dentures to the lingual side of the crest of the ridge of the lower jaw or mandible. While this alignment may lend increased stability to the lower denture, the tongue of the denture wearer can become crimped, leading to speech problems and eating difficulties. To avoid these problems, other dental professionals align the artificial teeth of lower dentures to the buccal side of the apex of the mandibular ridge. However, in this alignment the lower denture remains susceptible to tipping and dislodging when pressure is selectively applied near the buccal edge of the chewing surface of the lower molars. Because of this susceptibility to tipping and dislodging, buccal side alignment may require substantial occlusal adjustments to obtain a satisfactory fit.

Dentures typically demonstrate approximately 40% of the biting and chewing efficiency of natural teeth. To compensate for this decreased efficiency, dentures have been made wholly or partially of metal. Metal has been found to be particularly useful in providing a hardened cutting edge to increase cutting efficiency. However, the metal components are often embedded in dentures in complex patterns, making such dentures expensive to manufacture. These complex designs are susceptible to trapping food during mastication. In addition, the more complex metal cutting edge patterns can require increased training of the dental professional to learn how to correctly install such dentures. Even with additional training, multiple occlusal adjustments may be required to achieve a satisfactory fit with such dentures.

In other metal dentures, a metal insert or frame substitutes for porcelain or other life-like artificial teeth. Such metal inserts present obvious cosmetic problems. In addition, exposed, sharpened cutting edges of such metal inserts can injure the tongue and cheek of the denture wearer. To date, metal dentures have failed to completely solve the many problems facing denture wearers.

It is against this background that the significant improvements and advancement of the present invention have taken place in the field of dentures.

SUMMARY OF THE INVENTION

In accordance with its major aspects, dentures of the present invention comprise at least one pair of opposing posterior upper and posterior lower artificial teeth. Each posterior upper artificial tooth is formed from a resilient material, preferably an acrylic material, and has a substantially flat masticating surface. Each posterior lower artificial tooth has a single longitudinal crest formed along the length of its masticating surface with a single, elongated metal blade embedded therein. One of the longitudinal edges of the metal blade is flush with this longitudinal crest of the posterior lower artificial tooth. The posterior lower artificial teeth of the dentures of the present invention are fitted so that with the lower dentures positioned in the mouth of the denture wearer, the metal blade and longitudinal crest are positioned directly over the crest of the ridge of the wearer's lower jaw.

The present invention provides for well fitting dentures which exhibit increased cutting efficiency, chewing efficiency, and stability, and which are self adjusting, thereby creating natural occlusions and minimizing adjustment sessions with the dental professional.

A more complete appreciation of the present invention and its scope can be obtained from understanding the accompanying drawings, which are briefly summarized below, the following detailed description of presently preferred embodiments of the invention, and the appended claims.

BRIEF DESCRIPTION OF THE DRAWINGS

FIG. 1 is a perspective view of improved dentures incorporating the present invention which includes an upper denture and a lower denture.

FIG. 2 is a perspective view of the upper denture shown in FIG. 1.

FIG. 3 is a schematic side elevation view of the upper and lower dentures shown in FIGS. 1 and 2, in place in the mouth of a denture wearer.

FIG. 4 is a section view of the upper and lower dentures shown in FIG. 3 taken substantially along the line 4—4 of FIG. 3.

FIG. 5 is a perspective view of an elongated metal blade which is incorporated in the lower denture shown in FIGS. 1, 3 and 4.

FIG. 6 is a perspective view of an alternative embodiment of a lower denture incorporating the present invention.

FIG. 7 is a perspective view of another alternative embodiment of a lower denture incorporating the present invention.

FIG. 8 is a perspective view of upper and lower plaster casts used to manufacture improved dentures incorporating the present invention.

FIG. 9 is a top view of the lower plaster cast shown in FIG. 8.

FIG. 10 is a perspective view of partially exploded dentures on the upper and lower plaster casts shown in FIGS. 8 and 9.

DETAILED DESCRIPTION

One embodiment of improved dentures 10 which exhibits increased cutting efficiency, chewing efficiency and stability, and which is self-adjusting, is shown in FIGS. 1 through 4. The dentures 10 include an upper denture 12 and an opposing lower denture 14. The upper denture 12, which includes one or more artificial upper teeth 13, rests against the denture wearer's upper gum 16 covering the denture wearer's upper jaw or maxilla 18. The lower denture 14, which contains one or more artificial lower teeth 15, rests on the denture wearer's lower gum 20 covering the lower jaw or mandible 22 of the denture wearer. Embedded in the artificial teeth 15 of the lower denture 14 is an elongated metal blade 24. Proper alignment of the metal blade 24 in the lower denture 14 relative to the denture wearer's mandible 22 makes possible the increased chewing efficiently, increased stability and optimum occlusion achieved with the improved dentures 10.

The upper artificial teeth 13 are mounted in the upper denture 12 in a conventional way in an upper plastic base 28. The upper plastic base 28 is colored to resemble the natural color of the denture wearer's gums. The artificial upper teeth 13 each have a masticating surface 30, a lingual surface 32 which substantially surrounds the denture wearer's hard palate, and a buccal surface 34 which faces the denture wearer's cheeks and upper lip. The upper artificial teeth 13 are classified as posterior upper teeth 36, meaning molars and bicuspids, and anterior upper teeth 38. The posterior upper teeth 36 of the present invention are preferably formed from a slightly resilient material, preferably an acrylic material and most preferably a high impact acrylic, with the upper masticating surface 30 of the posterior upper teeth 36 formed substantially flat.

The upper denture 12 has a substantially semicircular shape. This semicircular shape, which provides an extensive area of contact between the upper denture 12 and the upper gum 16, is substantially defined by the upper plastic base 28 which extends inwardly from the lingual surfaces 32 of each of the upper artificial teeth 13 and covers the hard palate of the denture wearer.

The artificial lower teeth 15 are mounted in a conventional way in a lower plastic base 42 of the lower denture 14. The lower plastic base 42 is also colored to resemble the natural color of the denture wearer's gums. The artificial lower teeth 15 each have a masticating surface 44, a lingual surface 46 which surrounds the denture wearer's tongue, and a buccal surface 48 which faces the denture wearer's cheeks and lower lip. The lower artificial teeth 15 are classified as posterior lower teeth 50, meaning molars and bicuspids, and anterior lower teeth 52.

In contrast to the semicircular shape of the upper denture 12, the lower denture 14 is substantially U-shaped. This shape is dictated by the presence of the denture wearer's tongue, which is positioned between opposing posterior lower teeth 50 and precludes extension of the lower plastic base 42 therebetween.

Certain features of the improved dentures 10 can best be understood with reference to features of the denture wearer's maxilla 18 and the mandible 22 and their orientation relative to each other. A semicircular ridge 54 formed in the maxilla 18 defines the lower edge of the maxilla 18 and encircles the denture wearer's hard palate. In an analogous manner, a semicircular ridge 56 of the mandible 22 defines the top edge of the mandible 22 and encircles the denture wearer's tongue. A reference plane A—A may be viewed as extending parallel to but slightly spaced apart from and positioned between the mandibular and maxillular ridges 56 and 54. When the upper and lower dentures 12 and 14 are in place in the mouth of denture wearer, the upper masticating surfaces 30 contact the lower masticating surfaces 44 substantially at the plane A—A, with mastication taking place substantially at the plane A—A.

The posterior lower teeth 50 are formed of either acrylic or porcelain. Formed in each posterior lower tooth 50 and extending upward is a single longitudinal crest 60, which preferably extends the length of each posterior lower tooth. Each longitudinal crest 60 is formed of a predetermined height so that during mastication, the longitudinal crest 60 meets the upper masticating surface 30 of the opposing posterior upper tooth 36 at the reference plane A—A. In addition to having a predetermined vertical displacement, each longitudinal crest 60 is strategically formed in the lower denture 14 to be parallel with and directly overlie the mandibular ridge 56.

The elongated metal blade 24 (FIG. 5) is embedded in the posterior lower teeth 50 of the lower denture 14. The blade 24 may span multiple posterior teeth, as is shown in FIGS. 1 and 3 or may be segmented into shorter, abutting blades 24' as are installed in the lower denture 14' shown in FIG. 6. Alternatively, separate elongated blades 24" may extend less than the length of individual posterior lower teeth so that the blades 24" of adjacent teeth do not touch, as shown in FIG. 7.

The elongated metal blade 24 (FIG. 5) is preferably made from gold or stainless steel. As used herein, the term "gold" includes pure gold, gold alloys suitable for use in dental applications, and so-called dental gold. The blade 24 is approximately two millimeters thick and is rectangular with a first longitudinal edge 62 and a second longitudinal edge 64. The elongated metal blade 24 is imbedded in the posterior lower tooth or teeth 50 with the longitudinal edge 62 flush with and supported by the longitudinal crest 60. Although the process of embedding the blade 24 in the lower denture 14 utilizes conventional denture manufacturing processes, the relative placement of the blade 24 in the posterior lower tooth or teeth 50 and the size and placement of the longitudinal crest 60 are not conventional.

Holes 65 are formed in the blade 24 and define passageways 66 therethrough. When the blade 24 is embedded in the posterior artificial lower teeth 50, the artificial tooth material is typically fluid and fills the passageways 66, thereby connecting the lingual half of the posterior lower teeth 50 with the buccal half of the posterior lower teeth 50. The links provided by the artificial tooth material within the passageways 66 prevents displacement of the blade 24 upward beyond the longitudinal crest 60 and maintains the blade 24 in proper position in the posterior lower teeth 50.

Alternatively, the blade 24 may be of a trapezoidal shape with the first longitudinal edge 62 slightly shorter than the second longitudinal edge 64 without any holes formed therein. In this configuration, upward displacement of the blade 24 beyond the longitudinal crest 60 is prevented by artificial tooth material covering opposing corners of the second longitudinal edge 64.

In order to achieve the benefits of the improved dentures 10 of the present invention, as shown in FIG. 4 the longitudinal crest 60 and the elongated metal blade 24 must be aligned directly over the apex 68 (FIG. 4) of the mandibular ridge 56 of the denture wearer for whom the dentures are being constructed. The longitudinal crest 60 and the longitudinal edge 62 of the elongated blade 24 must be positioned so that both lie within the reference plane A—A when the dentures 10 are in place in the denture wearer's mouth.

It is also important that the posterior lower teeth 50 of the improved dentures 10 contain only a single longitudinal crest 60 and a single elongated blade 24, without transverse ridges or transverse blades. Additional longitudinal ridges, longitudinal blades, transverse ridges and transverse blades are omitted because they can contribute to denture instability and malocclusion. It is also important that no longitudinal or transverse troughs of any significant depth be formed in the masticating surfaces 44 of the posterior lower teeth 50 of the improved dentures 10. Such troughs are avoided because they can also contribute to malocclusion and because food tends to collect within them.

When the longitudinal crest 60 and the elongated metal blade 24 are aligned as described above relative to the reference plane A—A and to the apex 68 of the mandibular ridge 56, and when the masticating surfaces 30 of the posterior upper teeth 36 are substantially flat, the dentures 10 are inherently stable. This stability is due to a number of factors. During mastication the upper masticating surface 30 of each posterior upper tooth 36 contacts the lower masticating surface 44 of the opposing posterior lower tooth 50 in the center of the lower posterior teeth 50 at the longitudinal crest 60 which directly overlies the apex 68 of the mandibular ridge 56. Because of this alignment, the force of mastication which is applied to the lower posterior teeth 50 is fully supported by the mandibular ridge 56. Moreover, because the longitudinal crest 60 is neither offset to the lingual side 46 nor offset to the buccal side 48 of the posterior lower teeth 50, but rather is in the center thereof the tendency to tip the lower denture 14 during mastication is avoided. In addition, the relatively flat upper masticating surfaces 30 prevents the upper denture 12 from unintentionally catching and displacing the lower denture 14.

When the posterior upper artificial teeth 36 are made of acrylic material, including the preferred high impact acrylic, the improved dentures 10 are substantially self-adjusting. This self-adjustment feature is due primarily to the natural formation of a longitudinal central fossa 69 along the upper masticating surfaces 30 by action of the elongated metal blade 24 during mastication. Because the central fossa 69 is naturally formed as the denture wearer uses the dentures 10, a natural centric relationship between opposing upper and lower posterior teeth 36 and 50 is more quickly achieved and a natural fit of the upper and lower dentures 12 and 14 is obtained, with the dentures 10 accommodating natural lateral movement without tipping or dislodging of the dentures 10.

In addition to achieving the benefits of self-adjustment when the posterior upper teeth 36 are manufactured from acrylic material, additional benefits are achieved when the acrylic material selected is a high impact acrylic. Because of the enhanced durability of high impact acrylics, the vertical dimension of the upper posterior teeth 36 is maintained for a longer period of time when the upper posterior teeth 36 are made from a high impact acrylic. By so maintaining the vertical dimension of the posterior upper teeth 36, efficient mastication continues to take place in the plane A—A during the life of the dentures 10 and replacement of the upper denture 12 may be delayed for 2–5 years beyond the date when the upper denture 12 would otherwise have to be replaced because of wear to the upper masticating surfaces 30.

The self-adjusting feature of the improved dentures 10 minimizes the need for adjustment appointments with the dental professional. Excessive training of dental professionals is also minimized because the critical dimensions of the improved dentures are relatively easily specified. If, however, the upper teeth 13 are formed of porcelain, additional adjustments may be necessary to fit the upper and lower dentures 12 and 14 and additional training of the dental professional may be required.

Chewing efficiency is increased significantly with the improved dentures 10 because of the strategic position of the longitudinal blade 24 contacting the central fossa 69 naturally formed in the upper masticating surfaces 30. Increased chewing efficiency, results, in part, because of the strength of the metal blade 24. Increased chewing efficiency also results from the increased chewing force the denture wearer applies with the dentures 10 during mastication because of the confidence the denture wearer has that the lower denture 14 will be well supported by the mandibular ridge 56 and will not tip or dislodge. Problems traditionally associated with an exposed blade such as dulling of the exposed edge of such blades and injury to the denture wearer's tongue and cheek are avoided because the elongated blade 24 is laterally supported by artificial tooth material of the longitudinal ridge 60.

The combination of features of the present invention may not only be utilized in full mouth dentures as are shown in FIGS. 1–4 and 6, they also may be utilized in partial dentures 70 as is shown in FIG. 7. The improved partial dentures 70 shown in FIG. 7 include a pair of opposing upper and lower posterior teeth 72 and 74. The teeth 72 and 74 are attached to adjacent teeth by means of bridges 76 and 78. While other means of attachment may be employed, it is important to maintain the features of the applicant's invention, i.e., a flat upper masticating surface 80 in each posterior upper tooth 72, a single longitudinal crest 82 in each posterior lower tooth 74, alignment of the longitudinal crest 82 over the apex of the denture wearer's mandibular ridge (not shown), and contact of the elongated metal blade 24" and the longitudinal crest 82 with the upper masticating surface 80 at the plane in which mastication takes place. As mentioned above, the elongated blade 24" may be segmented (FIG. 7) or continuous along adjacent posterior lower teeth. Either way, the self-adjusting feature of the dentures 70 exhibit the increased cutting efficiency, chewing efficiency and stability, and minimization of sore sports experienced with the full mouth dentures 10 of the present invention.

In order to obtain the benefits described above with the improved dentures of the present invention, each denture set is custom manufactured for a particular denture wearer. In order to assemble the improved dentures 10 for a particular denture wearer from whom all teeth have been previously extracted, impressions are taken of the denture wearer's upper and lower jaws with conventional rubber-base, silicone-base, or water-base impression material. An upper plaster cast 101 and a lower plaster cast 102, shown in FIGS. 8–10, are fashioned from the impressions, using conventional techniques.

Formed in the lower plaster cast 102 is a lower ridge 103 having an apex 104. The lower ridge 103 is substantially the same shape and dimensions as the denture wearer's mandibular ridge as covered by the denture wearer's lower gum. Opposing rear portions 105 and 105' of the apex 104 define the portions of the lower ridge 103 which are analogous to the portions of the denture wearer's mandible in which the natural posterior lower teeth were previously attached. Also formed in the lower plaster cast 102 is a lower buccal edge 106, which marks the intersection of the denture wearer's cheek and mandible, and a lower lingual edge 107. The lower plaster cast 102 has a lower front portion 108 and opposing back portions 109 and 109'.

Formed in the upper plaster cast 101 is an upper ridge 113 having an apex 114. The upper ridge 113 is substantially the same shape and dimensions as the denture wearer's maxillular ridge as covered by the denture wearer's upper gum. Opposing rear portions 115 and 115' of the apex 114 define the portions of the ridge 113 which are analogous to the portions of the denture wearer's mandible in which the natural posterior upper teeth were previously attached. Also formed in the upper plaster cast 101 is an upper buccal edge 116.

Prior to assembly of components of the lower denture 14 using the lower plaster cast 102, lines B—B and B'—B' are drawn on the opposing rear portions 105 and 105' of the apex 104 of the lower ridge 103. Lines B—B and B'—B' are each substantially straight, when viewed from above, but follow the contour of the apex 104. Lines C—C and C'—C' are drawn on back portions 109 and 109', respectively, of the lower plaster cast 102. Line C—C generally extends perpendicularly downward from the posterior end of line B—B, with the lines C—C and B—B defining a reference plane D—D. Line C'—C' generally extends perpendicularly downward from the posterior end of line B'—B' with the lines C'—C' and B'—B' defining a reference plane D'—D' (FIG. 9). Lines E—E and E'—E' are drawn on the lower front portion 108 of the lower plaster cast 102 where the reference planes D—D and D'—D', respectively, intersect the lower front portion 108 of the lower plaster cast 102. A line F—F is also drawn on the lower plaster cast 102. The line F—F traces and connects the lower buccal and lingual edges 106 and 107, defining thereby a substantially U-shaped portion 110.

To assemble the lower denture 14, the U-shaped portion 110 of the lower plaster cast 102 is covered with a dental wax base 111 (FIG. 10). The dental wax base 111 is substantially opaque, obscuring the lines B—B and B'—B'. Anterior artificial lower teeth 52 are mounted in the dental wax base 111. Preferably the anterior artificial lower teeth 52 are substantially the same shape as the denture wearer's previous natural lower anterior teeth and are mounted in the dental wax base 111 in positions analogous to the previous positions of the natural lower anterior teeth. This similarity in shape and position to the denture wearer's natural teeth helps maintain the previously established relationships among the denture wearer's teeth, cheeks, tongue and lips. By manufacturing dentures which maintain these relationships, the dentures 10 give the denture wearer a natural, aesthetically acceptable appearance and retain the denture wearer's natural speech patterns.

A contiguous set 112 of posterior lower artificial teeth 50 in which a blade 24 has been previously embedded is mounted in the dental wax base 111 overlying the rear portion 105 of the lower ridge 103. Proper alignment of the set 112 is achieved by visually aligning the longitudinal edge 62 of the blade 24 along the lines C—C and E—E. Although the apex 104 of the ridge 103 may not be visible due to the opacity of the dental wax base 111, visual alignment of the longitudinal edge 62 of the blade 24 with the lines C—C and E—E results in alignment of the blade 24 directly over the apex 104. A contiguous set 112 of posterior lower teeth 50 in which a blade 24 has been previously embedded is similarly mounted in over rear portion 105' of the ridge 103, by alignment with lines C'—C' and E'—E'.

Predetermined, natural vertical dimensions of the posterior lower teeth 50 in the dental wax base 111 are maintained when setting the posterior lower teeth 50 into the dental was base 111. As a result of maintaining natural vertical dimensions, the upper and lower posterior teeth 36 and 50 contact each other in substantially the same place in the denture wearer's mouth as where the denture wearer's natural posterior teeth met.

Prior to assembly of components of the upper denture 12 using the upper plaster cast 101, a line G—G is drawn on the upper plaster cast 101. The line G—G traces and connects the upper buccal edges 116, defining thereby a substantially semicircular portion 120.

To assemble the upper denture 12, the semicircular portion 120 is covered with a dental wax plate 122 to the line G—G. Anterior artificial upper teeth 38 are mounted in the dental wax plate 122. Preferably the anterior artificial upper teeth 38 are substantially the same shape as the denture wearer's previous natural upper anterior teeth and are mounted in the dental wax plate 122 in positions analogous to the previous positions of the natural teeth. As mentioned above, maintenance of the previously established natural relationships among the denture wearer's teeth, cheeks, tongue and lips gives the denture wearer a more natural, aesthetically acceptable appearance while retaining the denture wearer's natural speech patterns.

Posterior upper artificial teeth 36 having substantially flat masticating surfaces 30 are then mounted in the dental wax plate 122 by centering each posterior upper tooth 36 over the apex 114 of the upper ridge 113. Typically, the location of the apex 114 is discernable without need for reference lines. Each posterior upper tooth 36 is inserted in the dental wax plate 122 to a predetermined depth so that each masticating surface 30 contacts the opposing lower posterior tooth 50 in the denture wearer's natural plane of mastication.

After mounting the upper and lower artificial teeth 13 and 15 in the denture wax plate 122 and denture wax base 111, respectively, the upper and lower plaster casts 101 and 102 are brought together to determine if the fit between upper and lower artificial teeth 13 and 15 creates an acceptable centric relationship. If alignment between the upper mastication surfaces 30 and the longitudinal crest 60 of the posterior lower teeth 50 is offset and therefore unacceptable, adjustments are preferably made to the placement of the posterior upper artificial teeth 13 in the dental wax plate 122 rather than to the posterior lower artificial teeth 15. Adjustments are made by moving the posterior upper teeth 36 either slightly to the buccal side or to the lingual side of the apex 114 of the upper ridge 113, as appropriate.

After proper placement of the upper and lower artificial teeth 13 and 15 in the dental wax plate 122 and dental wax base 111 is achieved, the dental wax plate and base 122 and 111 are replaced by acrylic material using conventional techniques. After manufacture of the dentures, fit of the dentures in the mouth of the denture wearer is checked. Any occlusal adjustments needed to achieve a proper equilibrium between the upper and lower dentures 12 and 14 should be made to the upper masticating surfaces 30 of the poster upper teeth 36 and not to the exposed elongated edge 62 of the elongated blade 24.

Presently preferred embodiments of the present invention and many improvements have been described with a degree of particularity. It should be understood that the present invention is defined by the spirit and scope of the following claims.

I claim:

1. Improved dentures for a denture wearer having a maxilla, a maxillular ridge, an upper gum covering said maxilla and maxillular ridge, a mandible, a mandibular ridge having an apex thereof, a lower gum covering said mandible and said mandibular ridge, and a reference plane between said mandibular ridge and said maxillular ridge in which mastication takes place, said improved dentures comprising:
   an upper denture adapted to be positioned on the upper gum and having at least one posterior upper artificial tooth formed therein;
   a substantially flat upper masticating surface formed in each posterior upper artificial tooth;
   a lower denture adapted to be positioned on the lower gum and opposing said upper denture, said lower denture having at least one posterior lower artificial tooth formed therein;
   a lower masticating surface formed in each posterior lower artificial tooth;
   a single, substantially longitudinal crest formed in and extending upward a predetermined height from said lower masticating surface, said longitudinal crest substantially centrally located on said lower masticating surface and positioned to be substantially parallel to and overlying the apex of the mandibular ridge; and
   an elongated metal blade having a longitudinal edge, said metal blade embedded in said at least one posterior lower artificial tooth with the longitudinal edge of the metal blade flush with and supported by the longitudinal crest.

2. The improved dentures of claim 1 wherein said at least one posterior upper tooth is resilient.

3. The improved dentures of claim 2 wherein said at least one posterior upper tooth is formed from acrylic material.

4. The improved dentures of claim 3 wherein said acrylic material is a high impact acrylic.

5. The improved dentures of claim 4 wherein said elongated blade is formed from gold.

6. The improved dentures of claim 5 wherein said upper denture includes at least two adjacent posterior upper teeth, said lower denture includes at least two adjacent posterior lower teeth, and said metal blade extends along the longitudinal crest of both said adjacent posterior lower teeth.

7. Improved dentures for a denture wearer having a maxilla, a maxillular ridge, an upper gum covering the maxilla and maxillular ridge, a mandible, a mandibular ridge having an apex, a lower gum covering the mandible, the mandibular ridge and the apex, and a reference plane between the mandibular ridge and the maxillular ridge in which mastication takes place, said improved dentures comprising:
   an upper denture adapted to be positioned on the upper gum and having a plurality of posterior upper artificial teeth formed therein;
   a substantially flat upper masticating surface formed in each posterior upper artificial tooth;
   a lower denture adapted to be positioned on the lower gum and opposing said upper denture, said lower denture having a plurality of lower right posterior artificial teeth and a plurality of lower left posterior artificial teeth formed therein;
   a lower masticating surface formed in each right and left posterior lower artificial tooth;
   a single, substantially longitudinal crest formed in and extending upward a predetermined height from each said lower masticating surface, said longitudinal crest positioned to be substantially parallel to and overlying the apex of the mandibular ridge; and a plurality of elongated metal blades, each said metal blade having a longitudinal edge and each said metal blade embedded in either a posterior right lower artificial tooth or a posterior left lower artificial tooth with the longitudinal edge of each metal blade flush with and supported by the longitudinal crest of said posterior lower right or left artificial tooth in which it is embedded.

8. The improved dentures of claim 7 wherein said posterior upper teeth are formed from an acrylic material.

9. The improved dentures of claim 8 wherein said acrylic material is a high impact acrylic.

10. The improved dentures of claim 9 wherein said elongated blade is formed from gold.

11. The improved dentures of claim 10 wherein a first said elongated metal blade is embedded in contiguous posterior lower right artificial teeth and a second said elongated metal blade is embedded in contiguous posterior lower left artificial teeth.

12. A method of manufacturing dentures having at least one posterior upper artificial tooth having a vertical dimension and a substantially flat masticating surface with a longitudinal center formed therein, at least one posterior lower artificial tooth having a longitudinal crest centrally formed therein, and an elongated blade embedded in said longitudinal crest, said dentures adapted to be worn by a denture wearer having a mandible, a mandibular ridge, a maxilla and a maxillular ridge, said method comprising the steps of:

aligning the elongated blade of each posterior lower tooth substantially parallel with and overlying the mandibular ridge of the denture wearer; and aligning the longitudinal center of the masticating surface of each posterior upper tooth substantially parallel with and overlying the maxillular ridge of the denture wearer.

13. The method of claim 12 further comprising the step of:

obtaining a predetermined occlusal relationship between each said posterior lower tooth, said elongated metal blade in each said posterior lower tooth, and a corresponding posterior upper tooth.

14. The method of claim 13 wherein the step of obtaining a predetermined occlusal relationship further comprises the step of:

adjusting the position of said each posterior upper tooth relative to a corresponding posterior lower tooth.

15. The method of claim 13 wherein the step of obtaining a predetermined occlusal relationship further comprises the step of:

adjusting the vertical dimension of said each posterior upper tooth.

16. The method of claim 12 further comprising the steps of:

forming an upper plaster cast of the maxilla, said upper plaster cast having an upper ridge formed therein;

forming a lower plaster cast of the mandible, said lower plaster cast having a back portion, a front portion and a lower ridge, said lower ridge having an apex and a rear portion;

extending a reference line from the apex of the rear portion of the lower ridge along the back portion and along the front portion of the lower plaster cast;

forming a lower wax base on the lower plaster cast;

mounting a posterior lower tooth with an elongated metal blade in the lower wax base in alignment with the reference line;

forming an upper wax plate on the upper plaster cast; and mounting a posterior upper tooth in the upper wax plate opposing said posterior lower tooth mounted in said lower wax base.

17. The method of claim 16 further comprising the step of:

obtaining a predetermined occlusal relationship between said each posterior lower tooth, said elongated metal blade in each said posterior lower tooth, and a corresponding posterior upper tooth.

18. The method of claim 17 wherein the step of obtaining a predetermined occlusal relationship further comprises the step of:

adjusting the position of each said posterior upper tooth relative to a corresponding posterior lower tooth.

19. The method of claim 17 wherein the step of obtaining a predetermined occlusal relationship further comprises the step of:

adjusting the vertical dimension of each said posterior upper tooth.

* * * * *